(12) United States Patent
Liu

(10) Patent No.: US 11,058,898 B2
(45) Date of Patent: Jul. 13, 2021

(54) NEUTRON CAPTURE THERAPY SYSTEM

(71) Applicant: NEUBORON MEDTECH LTD., Jiangsu (CN)

(72) Inventor: Yuanhao Liu, Jiangsu (CN)

(73) Assignee: NEUBORON MEDTECH LTD., Nanjing (CN)

( * ) Notice: Subject to any disclaimer, the term of this patent is extended or adjusted under 35 U.S.C. 154(b) by 0 days.

(21) Appl. No.: 16/745,565

(22) Filed: Jan. 17, 2020

(65) Prior Publication Data

US 2020/0155871 A1　May 21, 2020

Related U.S. Application Data

(63) Continuation of application No. PCT/CN2018/100753, filed on Aug. 16, 2018.

(30) Foreign Application Priority Data

Sep. 7, 2017　(CN) .......... 201710799364.4
Sep. 7, 2017　(CN) .......... 201710799911.9
Sep. 7, 2017　(CN) .......... 201710800745.X
Sep. 7, 2017　(CN) .......... 201710800921.X

(51) Int. Cl.
*A61N 5/10*　(2006.01)

(52) U.S. Cl.
CPC ......... *A61N 5/1077* (2013.01); *A61N 5/1064* (2013.01); *A61N 5/1071* (2013.01); *A61N 2005/109* (2013.01); *A61N 2005/1094* (2013.01)

(58) Field of Classification Search
None
See application file for complete search history.

(56) References Cited

U.S. PATENT DOCUMENTS

| 6,856,105 B2 | 2/2005 | Yao et al. |
| 2012/0253545 A1 | 10/2012 | Tachibana et al. |
| 2018/0236265 A1* | 8/2018 | Mukawa .................. A61N 5/10 |

FOREIGN PATENT DOCUMENTS

| CN | 102985981 A | 3/2013 |
| CN | 105120952 A | 12/2015 |
| CN | 106552322 A | 4/2017 |
| CN | 106975162 A | 7/2017 |

(Continued)

*Primary Examiner* — Hoon K Song
(74) *Attorney, Agent, or Firm* — Locke Lord LLP; Tim Tingkang Xia, Esq.

(57) ABSTRACT

A neutron capture therapy system includes an accelerator for accelerating charged particles to generate a charged particle beam, a beam transmitting device, and a neutron beam generating device. The neutron beam generating device further includes a first, a second and a third neutron beam generating device. The beam transmitting device further includes a first transmitting device connected to the accelerator, a beam direction conversion device configured to switch a traveling direction of the charged particle beam, and a second, a third and a fourth transmitting device that respectively transmit the charged particle beam from the beam direction conversion device to the first, the second and the third neutron beam generating device, wherein two of the first, the third and the fourth transmitting device define a first plane, a first and a second transmitting device define a second plane, and the first plane is different from the second plane.

17 Claims, 2 Drawing Sheets

(56) References Cited

FOREIGN PATENT DOCUMENTS

| | | |
|---|---|---|
| EP | 2364750 A1 | 9/2011 |
| EP | 2921206 A1 | 9/2015 |
| EP | 3032927 A1 | 6/2016 |
| JP | 2011182987 A | 9/2011 |
| JP | 2014161623 A | 9/2014 |
| JP | 2016107047 A | 6/2016 |
| TW | 201225112 A | 6/2012 |
| WO | 9415670 A1 | 7/1994 |

* cited by examiner

NEUTRON CAPTURE THERAPY SYSTEM

CROSS-REFERENCE TO RELATED PATENT APPLICATION

This application is a continuation application of International Application No. PCT/CN2018/100753, filed on Aug. 16, 2018, which claims priority to Chinese Patent Application No. 201710799364.4, filed on Sep. 7, 2017; Chinese Patent Application No. 201710800745.X, filed on Sep. 7, 2017; Chinese Patent Application No. 201710800921.X, filed on Sep. 7, 2017; and Chinese Patent Application No. 201710799911.9, filed on Sep. 7, 2017, the disclosures of which are hereby incorporated by reference.

FIELD

The present disclosure relates to a radiation irradiation system, and in particular to a neutron capture therapy system.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

As atomics moves ahead, such radiotherapy as Cobalt-60, linear accelerators and electron beams has been one of major means to cancer therapy. However, conventional photon or electron therapy has been undergone physical restrictions of radioactive rays; for example, many normal tissues on a beam path will be damaged as tumor cells are destroyed. On the other hand, sensitivity of tumor cells to the radioactive rays differs greatly, so in most cases, conventional radiotherapy falls short of treatment effectiveness on radioresistant malignant tumors (such as glioblastoma multiforme and melanoma).

For the purpose of reducing radiation damage to the normal tissue surrounding a tumor site, target therapy in chemotherapy has been employed in the radiotherapy. While for high-radioresistant tumor cells, radiation sources with high RBE (relative biological effectiveness) including such as proton, heavy particle and neutron capture therapy have also developed. Among them, the neutron capture therapy combines the target therapy with the RBE, such as the boron neutron capture therapy (BNCT). By virtue of specific grouping of boronated pharmaceuticals in the tumor cells and precise neutron beam regulation, BNCT is provided as a better cancer therapy choice than conventional radiotherapy.

Various radiations are generated during radiotherapy. For example, neutrons and photons of low-energy to high-energy are generated during boron neutron capture therapy. These radiations may cause different degrees of damage to normal human tissues. Therefore, in the field of radiotherapy, how to reduce radiation pollution to the external environment, medical staff or normal tissues of patients is an extremely important issue while effective treatment is achieved. Moreover, at present, in accelerator-based BNCT, a plurality of patients cannot be treated simultaneously, or a plurality of irradiation rooms are not appropriately arranged, resulting in a relatively long transmission path of a charged particle beam to cause a loss.

Therefore, it is necessary to propose a new technical solution to resolve the foregoing problem.

SUMMARY

To resolve the foregoing problem, an aspect of the present disclosure provides a neutron capture therapy system, including an accelerator, a beam transmitting device, and a neutron beam generating device, wherein the accelerator is configured to accelerate charged particles to generate a charged particle beam, the beam transmitting device is configured to transmit the charged particle beam generated by the accelerator to the neutron beam generating device, and the neutron beam generating device is configured to generate a therapeutic neutron beam. The neutron beam generating device further includes a first neutron beam generating device, a second neutron beam generating device, and a third neutron beam generating device. The beam transmitting device further includes a first transmitting device connected to the accelerator, a beam direction conversion device configured to switch a traveling direction of the charged particle beam, and a second transmitting device, a third transmitting device, and a fourth transmitting device that respectively transmit the charged particle beam from the beam direction conversion device to the first neutron beam generating device, the second neutron beam generating device, and the third neutron beam generating device, wherein two of the first transmitting device, the third transmitting device, and the fourth transmitting device define a first plane, the first transmitting device and the second transmitting device define a second plane, and the first plane is different from the second plane. In such an arrangement manner, space may be effectively utilized, a plurality of patients may be simultaneously treated, and a beam transmission path may not be excessively extended to ensure a small loss.

Implementations of this aspect may include one or more of the following features.

More particularly, the first transmitting device transmits the charged particle beam in an X-axis direction, and transmission directions of the third transmitting device and the fourth transmitting device are on an XY plane and form an angle greater than 0 degrees. Furthermore, the second transmitting device transmits the charged particle beam in a Z-axis direction, and the transmission directions of the third transmitting device and the fourth transmitting device and a transmission direction of the first transmitting device form a "Y" shape.

More particularly, the neutron capture therapy system further includes a treatment table, the neutron beam generating device includes a target, a beam shaping assembly, and a collimator, the target is disposed between the beam transmitting device and the beam shaping assembly, the charged particle beam generated by the accelerator is irradiated to the target through the beam transmitting device and interacts with the target to generate neutrons, and the generated neutrons sequentially pass through the beam shaping assembly and the collimator to form the therapeutic neutron beam to be irradiated to a patient on the treatment table.

Further, the beam shaping assembly includes a reflector, a moderator, a thermal neutron absorber, a radiation shield, and a beam exit, the moderator slows down the neutrons generated from the target to an epithermal neutron energy range, the reflector surrounds the moderator and guides deflected neutrons back to the moderator to increase the intensity of an epithermal neutron beam, the thermal neutron absorber is configured to absorb thermal neutrons to avoid overdosing in superficial normal tissue during treatment, the radiation shield is disposed at the rear of the reflector surrounding the beam exit, and is configured to shield against leaked neutrons and photons to reduce a dose to normal tissue in a non-irradiation area, the collimator is disposed at the rear of the beam exit to converge the neutron beam, a radiation shielding device is disposed between the patient and the beam exit to shield normal tissue of the patient from the radiation of beams from the beam exit. The beam transmitting device has a vacuum tube configured to accelerate or transmit the charged particle beam, the vacuum tube protrudes into the beam shaping assembly in the direction of the charged particle beam and sequentially passes through the reflector and the moderator, and the target is disposed in the moderator and is located at an end of the vacuum tube.

Further, the neutron capture therapy system further includes an irradiation room, the patient on the treatment table receives treatment of neutron beam irradiation in the irradiation room, the irradiation room includes a first irradiation room, a second irradiation room, and a third irradiation room that respectively correspond to the first neutron beam generating device, the second neutron beam generating device, and the third neutron beam generating device, and the first irradiation room, the second irradiation room, and the third irradiation room are respectively disposed in transmission directions of the second transmitting device, the third transmitting device, and the fourth transmitting device.

Furthermore, the neutron capture therapy system further includes a charged particle beam generation room, the charged particle beam generation room accommodates the accelerator and at least part of the beam transmitting device. The charged particle beam generation room includes an accelerator room and a beam transmission room, the first transmitting device extends from the accelerator room to the beam transmission room, at least part of the second neutron beam generating device and at least part of the third neutron beam generating device are respectively buried in partition walls that respectively separate the second irradiation room and the third irradiation room from the beam transmission room, the third transmitting device and the fourth transmitting device respectively extend from the beam transmission room to the second neutron beam generating device and the third neutron beam generating device, the first neutron beam generating device is located in the first irradiation room, the second transmitting device extends from the beam transmission room to the first irradiation room through the floor, and the neutron capture therapy system further includes a preparation room and a control room.

More particularly, the first neutron beam generating device, the second neutron beam generating device, and the third neutron beam generating device are respectively disposed along transmission directions of the second transmitting device, the third transmitting device, and the fourth transmitting device, directions of neutron beams generated by the first neutron beam generating device, the second neutron beam generating device, and the third neutron beam generating device are respectively the same as the transmission directions of the second transmitting device, the third transmitting device, and the fourth transmitting device, so that the directions of the neutron beams generated by the second neutron beam generating device and the third neutron beam generating device are on a same plane, and the direction of the neutron beam generated by the first neutron beam generating device is substantially perpendicular to the plane.

More particularly, the beam direction conversion device includes a first beam direction conversion assembly and a second beam direction conversion assembly, the beam transmitting device further includes a fifth transmitting device that connects the first beam direction conversion assembly and the second beam direction conversion assembly, the second transmitting device connects the first beam direction conversion assembly and the first neutron beam generating device, the third transmitting device connects the second beam direction conversion assembly and the second neutron beam generating device, and the fourth transmitting device connects the second beam direction conversion assembly and the third neutron beam generating device.

Further, each of the first beam direction conversion assembly and the second beam direction conversion assembly includes a deflection electromagnet for deflecting the charged particle beam and a switch electromagnet for controlling the traveling direction of the charged particle beam, the neutron capture therapy system further includes a beam dump configured to check an output of the charged particle beam before treatment, the first beam direction conversion assembly or the second beam direction conversion assembly guides the charged particle beam to the beam dump, each of the first transmitting device, the second transmitting device, the third transmitting device, the fourth transmitting device, and the fifth transmitting device includes a beam adjuster for the charged particle beam, and each of the second transmitting device, the third transmitting device, and the fourth transmitting device includes a current monitor and a charged particle beam scanner.

Another aspect of the present disclosure provides a neutron capture therapy system, including an accelerator, a beam transmitting device, and a first neutron beam generating device, where the accelerator is configured to accelerate charged particles to generate a charged particle beam, the beam transmitting device is configured to transmit the charged particle beam generated by the accelerator to the first neutron beam generating device, the first neutron beam generating device is configured to generate a therapeutic neutron beam, and a first shielding wall is disposed between the first neutron beam generating device and the accelerator to protect an operator from irradiation by neutrons and other radioactive rays leaked from the first neutron beam generating device during repair and maintenance of the accelerator and reduce reactions in which the accelerator is activated.

Implementations of this aspect may include one or more of the following features.

More particularly, the neutron capture therapy system further includes a treatment table, the first neutron beam generating device includes a target, a beam shaping assembly, and a collimator, the target is disposed between the beam transmitting device and the beam shaping assembly, the charged particle beam generated by the accelerator is irradiated to the target through the beam transmitting device and interacts with the target to generate neutrons, and the generated neutrons sequentially pass through the beam shaping assembly and the collimator to form the therapeutic neutron beam to be irradiated to a patient on the treatment table.

Further, the beam shaping assembly includes a reflector, a moderator, a thermal neutron absorber, a radiation shield, and a beam exit, the moderator slows down the neutrons generated from the target to an epithermal neutron energy range, the reflector surrounds the moderator and guides deflected neutrons back to the moderator to increase the intensity of an epithermal neutron beam, the thermal neutron absorber is configured to absorb thermal neutrons to avoid overdosing in superficial normal tissue during treatment, the radiation shield is disposed at the rear of the reflector surrounding the beam exit, and is configured to shield against leaked neutrons and photons to reduce a dose to normal tissue in a non-irradiation area, the collimator is disposed at the rear of the beam exit to converge the neutron beam, and a radiation shielding device is disposed between the patient and the beam exit to shield normal tissue of the patient from the radiation of beams from the beam exit.

Furthermore, the beam transmitting device has a vacuum tube configured to accelerate or transmit the charged particle beam, the vacuum tube protrudes into the beam shaping assembly in the direction of the charged particle beam and sequentially passes through the reflector and the moderator, and the target is disposed in the moderator and is located at an end of the vacuum tube.

More particularly, the neutron capture therapy system further includes a charged particle beam generation room and a first irradiation room, the charged particle beam generation room accommodates the accelerator and at least part of the beam transmitting device, a patient receives treatment of neutron beam irradiation in the first irradiation room, at least part of the first neutron beam generating device is buried in a first partition wall that separates the first irradiation room from the charged particle beam generation room, and the first shielding wall is disposed in the charged particle beam generation room.

Further, the charged particle beam generation room includes an accelerator room and a beam transmission room, the beam transmitting device includes a first transmitting device that is connected to the accelerator and extends from the accelerator room to the beam transmission room and a second transmitting device that extends from the beam transmission room to the first neutron beam generating device and transmits the charged particle beam to the first neutron beam generating device, the first partition wall is a partition wall that separates the first irradiation room from the beam transmission room, the first shielding wall is a partition wall between the accelerator room and the beam transmission room, and the first transmitting device passes through the first shielding wall.

Furthermore, the first transmitting device includes a first beam direction conversion assembly and a second beam direction conversion assembly configured to switch a traveling direction of the charged particle beam, a third transmitting device that connects the accelerator and the first beam direction conversion assembly, a fourth transmitting device that connects the first beam direction conversion assembly and the second beam direction conversion assembly, and a fifth transmitting device that connects the second transmitting device and the second beam direction conversion assembly, the first shielding wall is disposed between the accelerator and the first beam direction conversion assembly, and the third transmitting device passes through the first shielding wall; or the first shielding wall is disposed between the second beam direction conversion assembly and the first neutron beam generating device, and the fifth transmitting device passes through the first shielding wall; or the first shielding wall is disposed between the first beam direction conversion assembly and the second beam direction conversion assembly, and the fourth transmitting device passes through the first shielding wall. The neutron capture therapy system further includes a second neutron beam generating device and a second irradiation room, at least part of the second neutron beam generating device is buried in a second partition wall that separates the second irradiation room from the beam transmission room, the beam transmitting device further includes a sixth transmitting device that extends from the beam transmission room to the second neutron beam generating device and transmits the charged particle beam to the second neutron beam generating device, the first transmitting device further includes a seventh transmitting device that connects the sixth transmitting device and the second beam direction conversion assembly, when the first shielding wall is disposed between the second beam direction conversion assembly and the first neutron beam generating device, the seventh transmitting device also passes through the first shielding wall, each of the first beam direction conversion assembly and the second beam direction conversion assembly includes a deflection electromagnet for deflecting the charged particle beam and a switch electromagnet for controlling the traveling direction of the charged particle beam, the neutron capture therapy system further includes a beam dump configured to check an output of the charged particle beam before treatment, the first beam direction conversion assembly or the second beam direction conversion assembly guides the charged particle beam to the beam dump, each of the first transmitting device, the second transmitting device, and the sixth transmitting device includes a beam adjuster for the charged particle beam, and each of the second transmitting device and the sixth transmitting device includes a current monitor and a charged particle beam scanner.

Further, a second shielding wall is disposed between the first partition wall and the first shielding wall.

More particularly, a shielding door is disposed in the first shielding wall, and the shielding door includes a primary shielding door and a secondary shielding door or only includes a primary shielding door or secondary shielding door.

The third aspect of the present disclosure provides a neutron capture therapy system, including an accelerator, a beam transmitting device, and a first neutron beam generating device, the accelerator is configured to accelerate charged particles to generate a charged particle beam, the beam transmitting device is configured to transmit the charged particle beam generated by the accelerator to the first neutron beam generating device, the first neutron beam generating device is configured to generate a therapeutic neutron beam, the neutron capture therapy system further includes a charged particle beam generation room and a first irradiation room, the charged particle beam generation room is configured to accommodate the accelerator and at least part of the beam transmitting device, a patient receives treatment of neutron beam irradiation in the first irradiation room, at least part of the first neutron beam generating device is buried in a first partition wall that separates the first irradiation room from the charged particle beam generation room, a first shielding assembly is disposed at a position where the first neutron beam generating device passes on a side, facing the upstream of a beam transmission direction, of the first partition wall. The first shielding assembly is disposed, so that neutrons that overflow or are reflected from the first neutron beam generating device may be prevented from entering the charged particle beam generation room.

Implementations of this aspect may include one or more of the following features.

More particularly, the neutron capture therapy system further includes a treatment table, the first neutron beam generating device includes a target, a beam shaping assembly, and a collimator, the target is disposed between the beam transmitting device and the beam shaping assembly, the charged particle beam generated by the accelerator is irradiated to the target through the beam transmitting device and interacts with the target to generate neutrons, and the generated neutrons sequentially pass through the beam shaping assembly and the collimator to form the therapeutic neutron beam to be irradiated to the patient on the treatment table.

Further, the beam shaping assembly includes a reflector, a moderator, a thermal neutron absorber, a radiation shield, and a beam exit, the moderator slows down the neutrons generated from the target to an epithermal neutron energy range, the reflector surrounds the moderator and guides deflected neutrons back to the moderator to increase the intensity of an epithermal neutron beam, the thermal neutron absorber is configured to absorb thermal neutrons to avoid overdosing in superficial normal tissue during treatment, the radiation shield is disposed at the rear of the reflector surrounding the beam exit, and is configured to shield against leaked neutrons and photons to reduce a dose to normal tissue in a non-irradiation area, the collimator is disposed at the rear of the beam exit to converge the neutron beam, and a radiation shielding device is disposed between the patient and the beam exit to shield normal tissue of the patient from the radiation of beams from the beam exit.

Furthermore, the beam transmitting device has a vacuum tube configured to accelerate or transmit the charged particle beam, the vacuum tube protrudes into the beam shaping assembly in the direction of the charged particle beam and sequentially passes through the reflector and the moderator, and the target is disposed in the moderator and is located at an end of the vacuum tube.

More particularly, the beam transmitting device includes a first transmitting device connected to the accelerator, a beam direction conversion device configured to convert a traveling direction of the charged particle beam, and a second transmitting device configured to transmit the charged particle beam to the first neutron beam generating device, the second transmitting device passes through the first shielding assembly to reach the first neutron beam generating device, and the first shielding assembly covers an end, facing the accelerator, of the first neutron beam generating device and is in contact with the first partition wall around the first neutron beam generating device.

Further, the charged particle beam generation room includes an accelerator room and a beam transmission room, the first transmitting device extends from the accelerator room to the beam transmission room and passes through a second partition wall that separates the accelerator room from the beam transmission room, a second shielding assembly is disposed at a position where the first transmitting device passes on a side, facing the upstream of the beam transmission direction, of the second partition wall, the first transmitting device passes through the second shielding assembly and the second partition wall, and the second shielding assembly is in contact with the second partition wall around the first transmitting device. The second shielding assembly is disposed, so that neutrons that overflow or are reflected from the first transmitting device may be prevented from entering the accelerator room.

Furthermore, the neutron capture therapy system further includes a second irradiation room and a second neutron beam generating device that is located in the second irradiation room, the beam transmitting device includes a third transmitting device configured to transmit the charged particle beam to the second neutron beam generating device, the third transmitting device extends from the beam transmission room to the second irradiation room and passes through a third partition wall that separates the beam transmission room from the second irradiation room, a third shielding assembly is disposed at a position where the third transmitting device passes on a side, facing the upstream of the beam transmission direction, of the third partition wall, the third transmitting device passes through the third shielding assembly and the third partition wall to reach the second neutron beam generating device, and the third shielding assembly is in contact with the third partition wall around the third transmitting device. The third shielding assembly is disposed, so that neutrons that overflow or are reflected from the second irradiation room may be prevented from entering the beam transmission room.

Furthermore, transmission directions of the first transmitting device and the second transmitting device are on an XY plane, the third transmitting device transmits the charged particle beam in a Z-axis direction, and the third partition wall is the floor of the beam transmission room or the second irradiation room.

Furthermore, the beam direction conversion device includes a first beam direction conversion assembly and a second beam direction conversion assembly, the neutron capture therapy system further includes a third irradiation room and the third neutron beam generating device that is at least partially buried in a fourth partition wall that separates the third irradiation room from the charged particle beam generation room, the beam transmitting device includes a fourth transmitting device configured to transmit the charged particle beam to the third neutron beam generating device and a fifth transmitting device that connects the first beam direction conversion assembly and the second beam direction conversion assembly, the first transmitting device branches into the third transmitting device and the fifth transmitting device in the first beam direction conversion assembly, the fifth transmitting device branches into the second transmitting device and the fourth transmitting device in the second beam direction conversion assembly, a fourth shielding assembly is disposed at a position where the third neutron beam generating device passes on a side, facing the upstream of the beam transmission direction, of the fourth partition wall, the fourth transmitting device passes through the fourth shielding assembly to reach the third neutron beam generating device, and the fourth shielding assembly covers an end, facing the accelerator, of the third neutron beam generating device and is in contact with the fourth partition wall around the third neutron beam generating device. The fourth shielding assembly is disposed, so that neutrons that overflow or are reflected from the third neutron beam generating device can be prevented from entering the charged particle beam generation room. The first transmitting device and the fifth transmitting device transmit the charged particle beam in an X-axis direction, and the transmission direction of the second transmitting device and a transmission direction of the fourth transmitting device are on the XY plane and form a "Y" shape with the transmission direction of the first transmitting device. In such an arrangement manner, space may be effectively utilized, a plurality of patients may be simultaneously treated, and a beam transmission path may not be excessively extended to ensure a small loss.

The fourth aspect of the present disclosure provides a neutron capture therapy system, including an accelerator, a beam transmitting device, and a neutron beam generating device, wherein the accelerator is configured to accelerate charged particles to generate a charged particle beam, the beam transmitting device is configured to transmit the charged particle beam generated by the accelerator to the neutron beam generating device, the neutron beam generating device is configured to generate a therapeutic neutron beam, the neutron capture therapy system further includes an accelerator room, a beam transmission room, and an irradiation room, the accelerator room is configured to accommodate the accelerator, the beam transmission room is configured to at least partially accommodate the beam transmitting device, a patient receives treatment of neutron beam irradiation in the irradiation room, the beam transmitting device passes through a first partition wall that separates the accelerator room from the beam transmission room and/or a second partition wall that separates the beam transmission room from the irradiation room, and shielding assemblies are disposed at positions where the beam transmitting device passes on sides, facing the upstream of a beam transmission direction, of the first partition wall and/or the second partition wall. The shielding assemblies are disposed, so that neutrons that overflow or are reflected from the beam transmitting device and/or the irradiation room may be prevented from entering the accelerator room and/or the beam transmission room.

The fifth aspect of the present disclosure provides a neutron capture therapy system, including an accelerator, a beam transmitting device, and a neutron beam generating device, where the accelerator is configured to accelerate charged particles to generate a charged particle beam, the beam transmitting device is configured to transmit the charged particle beam generated by the accelerator to the neutron beam generating device, the neutron beam generating device is configured to generate a therapeutic neutron beam, and the beam transmitting device includes a shielding assembly for preventing neutrons and other radioactive rays from leaking from the beam transmitting device.

Implementations of this aspect may include one or more of the following features.

More particularly, the neutron capture therapy system further includes a treatment table, the neutron beam generating device includes a target, a beam shaping assembly, and a collimator, the target is disposed between the beam transmitting device and the beam shaping assembly, the charged particle beam generated by the accelerator is irradiated to the target through the beam transmitting device and interacts with the target to generate neutrons, and the generated neutrons sequentially pass through the beam shaping assembly and the collimator to form the therapeutic neutron beam to be irradiated to a patient on the treatment table.

Further, the beam shaping assembly includes a reflector, a moderator, a thermal neutron absorber, a radiation shield, and a beam exit, the moderator slows down the neutrons generated from the target to an epithermal neutron energy range, the reflector surrounds the moderator and guides deflected neutrons back to the moderator to increase the intensity of an epithermal neutron beam, the thermal neutron absorber is configured to absorb thermal neutrons to avoid overdosing in superficial normal tissue during treatment, the radiation shield is disposed at the rear of the reflector surrounding the beam exit, and is configured to shield against leaked neutrons and photons to reduce a dose to normal tissue in a non-irradiation area, the collimator is disposed at the rear of the beam exit to converge the neutron beam, and a radiation shielding device is disposed between the patient and the beam exit to shield normal tissue of the patient from the radiation of beams from the beam exit.

Furthermore, the beam transmitting device has a vacuum tube configured to accelerate or transmit the charged particle beam, the vacuum tube protrudes into the beam shaping assembly in the direction of the charged particle beam and sequentially passes through the reflector and the moderator, and the target is disposed in the moderator and is located at an end of the vacuum tube.

More particularly, the beam transmitting device includes a first transmitting device connected to the accelerator, a beam direction conversion device configured to switch a traveling direction of the charged particle beam, and a second transmitting device configured to transmit the charged particle beam to the neutron beam generating device, and the shielding assembly is a shielding cover surrounding the beam direction conversion device.

Further, the beam direction conversion device includes a first beam direction conversion assembly and a second beam direction conversion assembly, the beam transmitting device further includes a third transmitting device that connects the first beam direction conversion assembly and the second beam direction conversion assembly, and the shielding cover is two cover bodies that respectively surround the first beam direction conversion assembly and the second beam direction conversion assembly.

Furthermore, each of the first beam direction conversion assembly and the second beam direction conversion assembly includes a deflection electromagnet for deflecting the charged particle beam and a switch electromagnet for controlling the traveling direction of the charged particle beam, the neutron capture therapy system further includes a beam dump configured to check an output of the charged particle beam before treatment, the first beam direction conversion assembly or the second beam direction conversion assembly guides the charged particle beam to the beam dump, each of the first transmitting device, the second transmitting device, and the third transmitting device includes a beam adjuster for the charged particle beam, and the second transmitting device includes a current monitor and a charged particle beam scanner. The neutron beam generating device includes three neutron beam generating device, the second transmitting device includes a fourth transmitting device, a fifth transmitting device, and a sixth transmitting device that respectively transmit the charged particle beam to the three neutron beam generating device, the first transmitting device branches into the third transmitting device and the fourth transmitting device in the first beam direction conversion assembly, and the third transmitting device branches into the fifth transmitting device and the sixth transmitting device in the second beam direction conversion assembly.

Further, the neutron capture therapy system further includes a charged particle beam generation room and an irradiation room, the charged particle beam generation room accommodates the accelerator and at least part of the beam transmitting device, a patient receives treatment of neutron beam irradiation in the irradiation room, and at least part of the neutron beam generating device is buried in a partition wall that separates the irradiation room from the charged particle beam generation room.

Furthermore, the charged particle beam generation room includes an accelerator room and a beam transmission room, the first transmitting device extends from the accelerator room to the beam transmission room, the second transmitting device extends from the beam transmission room to the neutron beam generating device, and the beam direction conversion device and the shielding cover are accommodated in the beam transmission room.

By means of the neutron capture therapy system in the present disclosure, space may be effectively utilized, a plurality of patients may be simultaneously treated, and a beam transmission path may not be excessively extended to ensure a small loss.

Further areas of applicability will become apparent from the description provided herein. It should be understood that the description and specific examples are intended for purposes of illustration only and are not intended to limit the scope of the present disclosure.

BRIEF DESCRIPTION OF THE DRAWINGS

The accompanying drawings illustrate one or more embodiments of the disclosure and together with the written description, serve to explain the principles of the disclosure. Wherever possible, the same reference numbers are used throughout the drawings to refer to the same or like elements of an embodiment.

DETAILED DESCRIPTION OF THE DISCLOSURE

The embodiments of the present disclosure are further described in detail below with reference to the accompanying drawings, so that those skilled in the art can implement the technical solutions according to the description. An XYZ coordinate system (referring to FIG. 2 and FIG. 3) in which a direction of a charged particle beam P emitted by an accelerator is used as an X-axis direction, a direction orthogonal to the direction of the charged particle beam P emitted by the accelerator is used as a Y-axis direction, and a direction perpendicular to the ground is used as a Z-axis direction is set below, and X, Y, and Z are used in the description of position relationships between various constituent elements.

Figure 1:
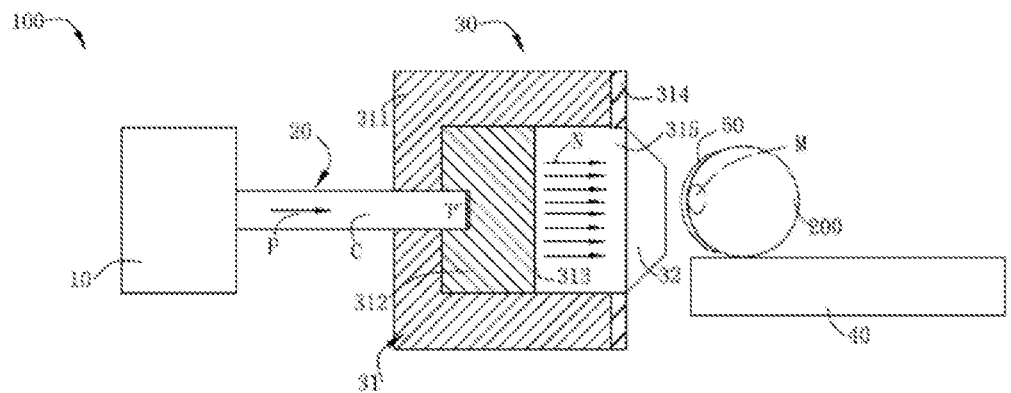
FIG. 1 is a schematic structural diagram of a neutron capture therapy system according to an embodiment of the present disclosure.

As shown in FIG. 1, a neutron capture therapy system in this embodiment is preferably a boron neutron capture therapy system 100. The boron neutron capture therapy system 100 is an apparatus using BNCT to treat cancer. In BNCT, a patient 200 injected with boron (B-10) is irradiated with a neutron beam N to treat cancer. After the patient 200 is administrated or injected boron (B-10)-containing pharmaceuticals, the boron-containing pharmaceuticals selectively accumulates in the tumor cell M, and then takes advantage that the boron (B-10)-containing pharmaceuticals have high neutron capture cross section and produces $^4$He and $^7$Li heavy charged particles through $^{10}$B(n,$\alpha$)$^7$Li neutron capture and nuclear fission reaction. The two charged particles, with average energy at about 2.33 MeV, are of high linear energy transfer (LET) and short-range characteristics. LET and range of the alpha particle are 150 keV/micrometer and 8 micrometers respectively while those of the heavy charged particle $^7$Li are 175 keV/micrometer and 5 micrometers respectively, and the total range of the two particles approximately amounts to a cell size. Therefore, radiation damage to living organisms may be restricted at the cells' level, only the tumor cells will be destroyed on the premise of having no major normal tissue damage.

The boron neutron capture therapy system 100 includes an accelerator 10, a beam transmitting device 20, a neutron beam generating device 30, and a treatment table 40. The accelerator 10 accelerates charged particles (such as protons and deuterons) to generate a charged particle beam P such as a proton beam. The beam transmitting device 20 transmits the charged particle beam P generated by the accelerator 10 to the neutron beam generating device 30. The neutron beam generating device 30 generates a therapeutic neutron beam N to be irradiated to the patient 200 on the treatment table 40.

The neutron beam generating device 30 includes a target T, a beam shaping assembly 31, and a collimator 32. The charged particle beam P generated by the accelerator 10 is irradiated to the target T by the beam transmitting device 20 and interacts with the target T to generate neutrons, and the generated neutrons sequentially pass through the beam shaping assembly 31 and the collimator 32 to form the therapeutic neutron beam N to be irradiated to the patient 200 on the treatment table 40. The target T is preferably a metal target. Suitable nuclear reactions are selected according to characteristics such as desired neutron yield and energy, available accelerated charged particle energy, and current and materialization of the metal target. The most discussed two nuclear reactions are $^7$Li(p,n)$^7$Be and $^9$Be(p,n)$^9$B and are both endothermic reactions. Energy thresholds of the two nuclear reactions are respectively 1.881 MeV and 2.055 MeV. Epithermal neutrons at a keV energy level are considered ideal neutron sources for BNCT. Theoretically, if a lithium metal target is bombarded with protons with energy slightly higher than the thresholds, neutrons relatively low in energy can be generated, and can be used clinically without many moderations. However, both a lithium metal (Li) target and a beryllium metal (Be) target and protons of threshold energy exhibit moderately low reaction cross sections. To generate sufficient neutron fluxes, high-energy protons are usually chosen to trigger the nuclear reactions. An ideal target is supposed to have the characteristics of high neutron yield, a generated neutron energy distribution near an epithermal neutron energy range (see details below), moderate strong-penetration radiation, safety, low cost, easy accessibility, high temperature resistance, and the like. However, in reality, no nuclear reactions can satisfy all requests. The target T well known to a person skilled in the art may be made of a metal material other than Li and Be, for example, Ta or W or an alloy thereof. The accelerator 10 may be a linear accelerator, a cyclotron, a synchrotron, and a synchrocyclotron.

The beam shaping assembly 31 may adjust beam quality of the neutron beam N generated from the interaction between the charged particle beam P and the target T. The collimator 32 is configured to converge the neutron beam N to provide the neutron beam N with relatively high targeting efficiency during treatment. The beam shaping assembly 31 further includes a reflector 311, a moderator 312, a thermal neutron absorber 313, a radiation shield 314, and a beam exit 315. Neutrons generated from the interaction between the charged particle beam P and the target T have a very wide energy spectrum, among which epithermal neutrons meet therapeutic requirements, and the content of other types of neutrons and photons needs to be minimized to avoid harm to an operator or a patient. Therefore, the neutrons from the target T need to pass through the moderator 312 to adjust the energy (>40 keV) of fast neutrons into an epithermal neutron energy range (0.5 eV to 40 keV) and reduce thermal neutrons (<0.5 eV) as much possible. The moderator 312 is made of a material having a cross section for principally acting with fast neutrons but hardly acting with epithermal neutrons. In this embodiment, the moderator 312 is made of at least one of $D_2O$, $AlF_3$, Fluental™, $CaF_2$, $Li_2CO_3$, $MgF_2$, and $Al_2O_3$. The reflector 311 surrounds the moderator 312 and reflects neutrons that pass through the moderator 312, so the neutrons are scattered back to the neutron beam N to increase the utilization of neutrons. The reflector 311 is made of a material with high neutron reflection ability. In this embodiment, the reflector 311 is made of at least one of Pb or Ni. The thermal neutron absorber 313 is disposed at the rear of the moderator 312, and is made of a material with a large thermal neutron reaction cross section. In this embodiment, the thermal neutron absorber 313 is made of Li-6. The thermal neutron absorber 313 is configured to absorb thermal neutrons that pass through the moderator 312 to reduce the content of thermal neutrons in the neutron beam N so as to avoid overdosing in superficial normal tissue during treatment. The radiation shield 314 is disposed at the rear of the reflector surrounding the beam exit 315, and is configured to shield against neutrons and photons that are leaked from a part except the beam exit 315. The material of the radiation shield 314 includes at least one of a photon shielding material and a neutron shielding material. In this embodiment, the material of the radiation shielding 314 includes a photon shielding material being lead (Pb) and a neutron shielding material being polyethylene (PE). It should be understood that the beam shaping assembly 31 may further have another structure, provided that an epithermal neutron beam required for treatment can be obtained. The collimator 32 is disposed at the rear of the beam exit 315. The epithermal neutron beam from the collimator 32 is irradiated to the patient 200, and is moderated by superficial normal tissue to thermal neutrons to reach tumor cells M. It should be understood that the collimator 32 may be alternatively omitted or replaced with another structure. The neutron beam from the beam exit 315 is directly irradiated to the patient 200. In this embodiment, a radiation shielding device 50 is further disposed between the patient 200 and the beam exit 315 to shield normal tissue of the patient from irradiation by the beam from the beam exit 315. It should be understood that the radiation shielding device 50 may not be disposed. The target T is disposed between the beam transmitting device 20 and the beam shaping assembly 31. The beam transmitting device 20 has a vacuum tube C configured to accelerate or transmit the charged particle beam P. In this embodiment, the vacuum tube C protrudes into the beam shaping assembly 31 in the direction of the charged particle beam P and sequentially passes through the reflector 311 and the moderator 312. The target T is disposed in the moderator 312 and is located at an end of the vacuum tube C, to achieve relatively good neutron beam quality. It should be understood that the target may be disposed in another manner, and may also be movable with respect to the accelerator or the beam shaping assembly, to facilitate target replacement or uniform interaction between the charged particle beam and the target.

Figure 2:
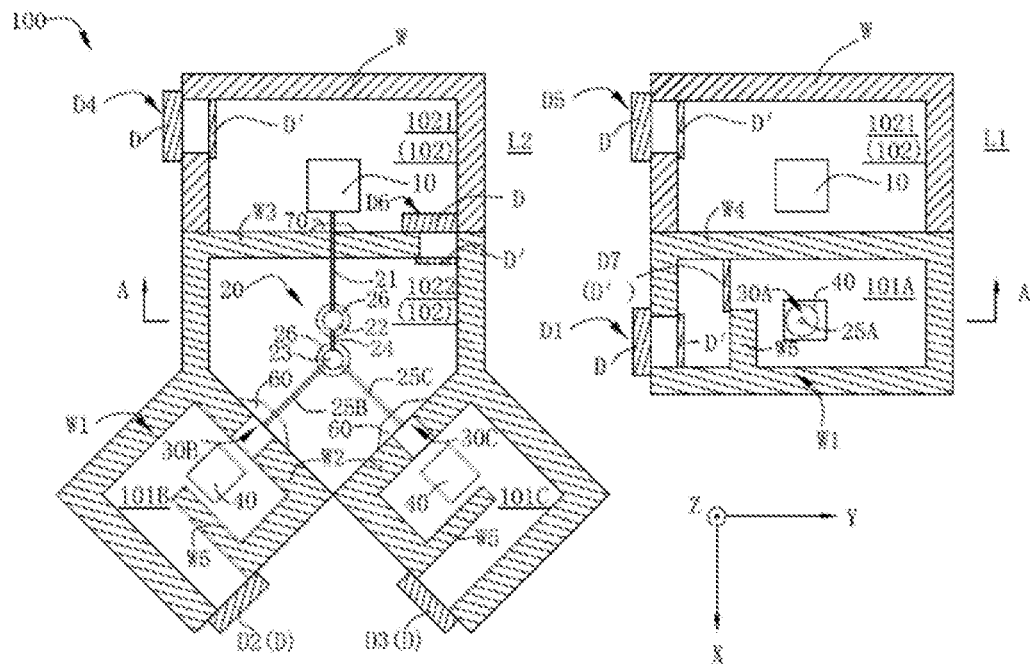
FIG. 2 is a schematic layout diagram of a neutron capture therapy system on an XY plane according to an embodiment of the present disclosure.
Figure 3:
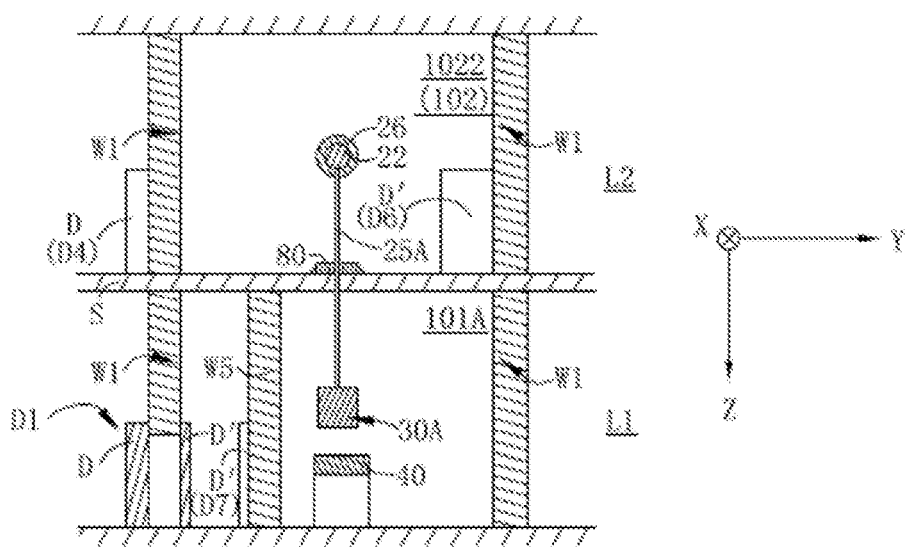
FIG. 3 is a schematic diagram of a section A-A in FIG. 2.

Referring to FIG. 2 and FIG. 3, the entire boron neutron capture therapy system 100 is arranged in the space of two floors L1 and L2. The boron neutron capture therapy system 100 further includes an irradiation room 101 (101A, 101B, 101C) and a charged particle beam generation room 102. The patient 200 on the treatment table 40 is treated by irradiation with the neutron beam N in the irradiation room 101 (101A, 101B, 101C). The charged particle beam generation room 102 accommodates the accelerator 10 and at least part of the beam transmitting device 20. The neutron beam generating device 30 may include one neutron beam generating device or a plurality of neutron beam generating devices, to generate one or more therapeutic neutron beams N. The beam transmitting device 20 may selectively transmit the charged particle beam P to one or more neutron beam generating devices or synchronously transmit the charged particle beam P to the plurality of neutron beam generating devices. Each neutron beam generating device corresponds to one irradiation room 101. In this embodiment, there are three neutron beam generating devices, namely, a neutron beam generating device 30A, a neutron beam generating device 30B, a neutron beam generating device 30C, and three irradiation rooms, namely, an irradiation room 101A, an irradiation room 101B, and an irradiation room 101C. The beam transmitting device 20 includes: a first transmitting device 21, connected to the accelerator 10; a first beam direction conversion assembly 22 and a second beam direction conversion assembly 23 that are configured to convert a traveling direction of the charged particle beam P; a second transmitting device 24, connecting the first beam direction conversion assembly 22 and the second beam direction conversion assembly 23; a third transmitting device 25A, a fourth transmitting device 25B, and a fifth transmitting device 25C that are configured to respectively transmit the charged particle beam P from the first beam direction conversion assembly 22 or the second beam direction conversion assembly 23 to the neutron beam generating device 30A, the neutron beam generating device 30B, and the neutron beam generating device 30C. The generated neutron beam N is then respectively irradiated to patients in the irradiation room 101A, the irradiation room 101B, and the irradiation room 101C. The third transmitting device 25A connects the first beam direction conversion assembly 22 and the neutron beam generating device 30A, the fourth transmitting device 25B connects the second beam direction conversion assembly 23 and the neutron beam generating device 30B, and the fifth transmitting device 25C connects the second beam direction conversion assembly 23 and the neutron beam generating device 30C. That is, the first transmitting device 21 branches into the second transmitting device 24 and the third transmitting device 25A in the first beam direction conversion assembly 22. The second transmitting device 24 then branches into the fourth transmitting device 25B and the fifth transmitting device 25C in the second beam direction conversion assembly 23. The first transmitting device 21 and the second transmitting device 24 transmit in an X-axis direction. The third transmitting device 25A transmits the charged particle beam in a Z-axis direction. The transmission directions of the fourth transmitting device 25B and the fifth transmitting device 25C are on an XY plane and form a "Y" shape with the transmission direction of the first transmitting device 21 and the second transmitting device 24. The neutron beam generating device 30A, the neutron beam generating device 30B, and the neutron beam generating device 30C and the corresponding irradiation room 101A, irradiation room 101B, and irradiation room 101C are respectively disposed along the transmission directions of the third transmitting device 25A, the fourth transmitting device 25B, and the fifth transmitting device 25C. Directions of generated neutron beams N are respectively the same as the transmission directions of the third transmitting device 25A, the fourth transmitting device 25B, and the fifth transmitting device 25C, so that directions of neutron beams generated by the neutron beam generating device 30B and the neutron beam generating device 30C are on a same plane, and the direction of the neutron beam generated by the neutron beam generating device 30A is substantially perpendicular to the plane. In such an arrangement manner, space may be effectively utilized, a plurality of patients may be simultaneously treated, and a beam transmission path may not be excessively extended to ensure a small loss. It should be understood that the direction of the neutron beam N generated by the neutron beam generating device 30A (30B, 30C) may be alternatively different from the transmission direction of the third (fourth, fifth) transmitting device 25A (25B, 25C). The transmission directions of the first transmitting device 21 and the second transmitting device 24 may be alternatively different. The second transmitting device 24 may further be omitted, and only one beam direction conversion assembly is used to branch the beam into two or more transmission portions. The transmission directions of the fourth transmitting device 25B and the fifth transmitting device 25C form a "Y" shape with the transmission direction of the first transmitting device 21 or may be a variation of "Y". For example, the transmission direction of the fourth transmitting device 25B or the fifth transmitting device 25C is the same as the transmission direction of the first transmitting device 21. The transmission directions of the fourth transmitting device 25B and the fifth transmitting device 25C may alternatively form another shape, for example, a "T" shape or an arrow shape, with the transmission direction of the first transmitting device 21, provided that the transmission directions of the fourth transmitting device 25B and the fifth transmitting device 25C form an angle greater than 0 degrees on the XY plane. The transmission directions of the fourth transmitting device 25B and the fifth transmitting device 25C may not be limited to the XY plane. The transmission direction of the third transmitting device 25A may alternatively be not in the Z-axis direction, provided that two of the transmission direction of the fourth transmitting device 25B, the transmission direction of the fifth transmitting device 25C, and the transmission direction of the first transmitting device 21 are on the same plane (a first plane). The transmission direction of the first transmitting device 21 and the transmission direction of the third transmitting device 25A are also on the same plane (a second plane), and the first plane is different from the second plane. The third transmitting device 25A, the neutron beam generating device 30A, and the irradiation room 101A may be alternatively omitted. In this case, the beam is transmitted only on the XY plane.

Each of the first beam direction conversion assembly 22 and the second beam direction conversion assembly 23 includes a deflection electromagnet for deflecting the charged particle beam P and a switch electromagnet for controlling the traveling direction of the charged particle beam P. The boron neutron capture therapy system 100 may further include a beam dump (not shown) configured to check an output of the charged particle beam P before treatment. The first beam direction conversion assembly 22 or the second beam direction conversion assembly 23 may cause the charged particle beam P to depart from a regular orbit and guide the charged particle beam to the beam dump.

The first transmitting device 21, the second transmitting device 24, the third transmitting device 25A, the fourth transmitting device 25B, and the fifth transmitting device 25C are all constructed by the vacuum tube C, and may be respectively formed by connecting a plurality of sub-transmitting devices. Transmission directions of the plurality of sub-transmitting devices may be the same or different. For example, the deflection electromagnet is used to deflect a beam transmission direction. The transmission directions of the first transmitting device 21, the second transmitting device 24, the third transmitting device 25A, the fourth transmitting device 25B, and the fifth transmitting device 25C may be respectively the transmission direction of any sub-transmitting device, where each of the formed first plane and second plane is a plane formed by a sub-transmitting device directly connected to the beam direction conversion assembly, and may respectively further include a beam adjuster (not shown) for the charged particle beam P. The beam adjuster includes a horizontal steering and a horizontal and vertical steering configured to adjust an beam axis of the charged particle beam P, a quadrupole electromagnet configured to suppress divergence of the charged particle beam P, a four-direction slit configured to shape the charged particle beam P, and the like. Each of the third transmitting device 25A, the fourth transmitting device 25B, and the fifth transmitting device 25C may include a current monitor (not shown) and a charged particle beam scanner (not shown) as required. The current monitor measures a current value (that is, an amount of charge, a radiation dose rate) of the charged particle beam P with which the target T is irradiated in real time. The charged particle beam scanner scans the charged particle beam P and controls irradiation of the target T with the charged particle beam P, for example, controls an irradiation position of the target T with the charged particle beam P.

The charged particle beam generation room 102 may include an accelerator room 1021 and a beam transmission room 1022. The accelerator room 1021 occupies two floors. The accelerator 10 extends from L2 to L1. The beam transmission room 1022 is located on L2. The first transmitting device 21 extends from the accelerator room 1021 to the beam transmission room 1022. The irradiation room 101B and the irradiation room 101C are located on L2. The irradiation room 101A is located on L1. In this embodiment, L1 is below L2. To be specific, the floor of L2 is the ceiling of L1. It should be understood that L1 and L2 may be exchanged. The material of the floor (ceiling) S may be concrete with a thickness greater than 0.5 m or boron-containing barite concrete. The irradiation room 101A, the irradiation room 101B, the irradiation room 101C, and the beam transmission room 1022 have shielded spaces surrounded by a shielding wall W1. The shielding wall W1 may be a wall that is made of boron-containing barite concrete and has a thickness greater than 1 m and a density of 3 g/c.c., and includes first partition shielding walls W2 that separates the beam transmission room 1022 from the irradiation room 101B and the irradiation room 101C, a second partition shielding wall W3 that separates the accelerator room 1021 from the beam transmission room 1022 on L1, and a third partition shielding wall W4 that separates the accelerator room 1021 from the irradiation room 101A on L2. The accelerator room 1021 is surrounded by a concrete wall W, the second partition shielding wall W3, and the third partition shielding wall W4 with a thickness greater than 1 m. At least part of the neutron beam generating device 30B and at least part of the neutron beam generating device 30C are buried in the first partition shielding wall W2. The fourth transmitting device 25B and the fifth transmitting device 25C respectively extend from the beam transmission room 1022 to the neutron beam generating device 30B and the neutron beam generating device 30C. The neutron beam generating device 30A is located in the irradiation room 101A, and the third transmitting device 25A extends from the beam transmission room 1022 to the irradiation room 101A through the floor S. The irradiation room 101A, the irradiation room 101B, and the irradiation room 101C respectively have shielding doors D1, D2, D3 for the treatment table 40 and doctors to pass. The accelerator room 1021 respectively has a shielding door D4 and a shielding door D5 on L1 and L2 for access to the accelerator room 1021 to maintain the accelerator 10. The beam transmission room 1022 has a shielding door D6 for access from the accelerator room 1021 to the beam transmission room 1022 to maintain the beam transmitting device 20. The shielding door D6 is disposed on the second partition shielding wall W3. Inner shielding walls W5 are further provided in the irradiation room 101A, the irradiation room 101B, and the irradiation room 101C to form labyrinth passages from the shielding door D1, the shielding door D2, and the shielding door D3 to beam exits, which may prevent direct irradiation of radioactive rays when the shielding door D1, the shielding door D2, and the shielding door D3 are open by accident. According to different layouts in irradiation rooms, the inner shielding walls W5 may be disposed at different positions. A shielding door D7 inside the irradiation room may further be disposed between the inner shielding wall W5 and the shielding wall W1 or the third partition shielding wall W4 to form secondary protection during treatment with neutron beam irradiation. The inner shielding wall W5 may be a wall that is made of a boron-containing barite concrete and has a thickness greater than 0.5 m and a density of 3 g/c.c. Each of the shielding door D1, the shielding door D2, the shielding door D3, the shielding door D4, the inner shielding door D5, the shielding door D6, and the shielding door D7 may include a primary shielding door D and a secondary shielding door D' that are independent of each other or may include only a primary shielding door D or a secondary shielding door D', which may be determined based on an actual case. The primary shielding door D may be made of the same material, for example, boron-containing PE or barite concrete or lead having a thickness greater than 0.5 m and a density of 6 g/c.c. The secondary shielding door D' may be made of the same material, for example, boron-containing PE or barite concrete or lead having a thickness greater than 0.2 m and a density of 6 g/c.c. In this embodiment, each of the shielding door D1, the shielding door D4, the shielding door D5, and the shielding door D6 includes the primary shielding door D and the secondary shielding door D', each of the shielding door D1, the shielding door D2, and the shielding door D3 includes only the primary shielding door D, and the shielding door D7 includes only the secondary shielding door D'. A shielding wall and a shielding door form a shielding space to suppress phenomena that radioactive rays enter the irradiation room 101A, the irradiation room 101B, the irradiation room 101C, and the beam transmission room 1022 from outside and leave these rooms. In this embodiment, the second partition shielding wall W3 that separates the accelerator room 1021 from the beam transmission room 1022 is disposed between the accelerator 10 and the first beam direction conversion assembly 22. That is, the first transmitting device 21 passes through the second partition shielding wall W3. It should be understood that the second partition shielding wall W3 and the shielding door D6 may be omitted or may be alternatively disposed at another position, for example, between the first beam direction conversion assembly 22 and the second beam direction conversion assembly 23 or between the second beam direction conversion assembly 23 and the neutron beam generating device 30B and the neutron beam generating device 30C. Alternatively, an additional partition shielding wall and shielding door is disposed between the second partition shielding wall W3 and the first partition shielding wall W2. That is, a shielding wall is disposed between the neutron beam generating device and the accelerator. During repair and maintenance of the accelerator, an operator is protected from irradiation by neutrons and other radioactive rays leaked from the neutron beam generating device, and the same time reactions in which the accelerator is activated by neutrons are reduced.

Neutrons and other radioactive rays tend to leak at a position where an assembly or element passing through a shielding wall or floor. For example, in this embodiment, the neutron beam generating device 30B and the neutron beam generating device 30C pass through the first partition shielding wall W2, the first transmitting device 21 passes through the second partition shielding wall W3, and the third transmitting device 25A passes through the floor S. A first shielding assembly 60, a second shielding assembly 70, and a third shielding assembly 80 may be respectively disposed at positions where the neutron beam generating device 30B, the neutron beam generating device 30C, the first transmitting device 21, and the third transmitting device 25A pass on sides, facing the upstream of the beam transmission direction, of the first partition shielding wall W2, the second partition shielding wall W3, and the floor S. The first shielding assembly 60 covers ends, facing the accelerator, of the neutron beam generating device 30B and the neutron beam generating device 30C and is in contact with the first partition shielding walls W2 around the neutron beam generating device 30B and the neutron beam generating device 30C, so that neutrons that overflow or are reflected from the beam shaping assemblies of the neutron beam generating device 30B and the neutron beam generating device 30C are prevented from entering the accelerator room 1021 and the beam transmission room 1022. The fourth transmitting device 25B and the fifth transmitting device 25C pass through the first shielding assembly 60 to reach the targets T of the neutron beam generating device 30B and the neutron beam generating device 30C. The second shielding assembly 70 is in contact with the second partition shielding wall W3 around the first transmitting device 21, so that neutrons that overflow or are reflected from the beam transmitting device 20 are prevented from entering the accelerator room 1021. The first transmitting device 21 passes through the second shielding assembly 70 and the second partition shielding wall W3 to reach the first beam direction conversion assembly 22. The third shielding assembly 80 is in contact with the floor S around the third transmitting device 25A, so that neutrons that overflow or are reflected from the irradiation room 101A are prevented from entering the beam transmission room 1022. The third transmitting device 25A passes through the third shielding assembly 80 and the floor S to reach the neutron beam generating device 30A. The materials of the first shielding assembly 60, the second shielding assembly 70, and the third shielding assembly 80 may be boron-containing PE or barite concrete or lead.

The first beam direction conversion assembly 22 and the second beam direction conversion assembly 23 are respectively surrounded by a shielding cover 26 to prevent neutrons and other radioactive rays from leaking from the beam direction conversion assembly. The material of the shielding cover 26 may be boron-containing PE or barite concrete or lead. It should be understood that the first beam direction conversion assembly 22 and the second beam direction conversion assembly 23 may be alternatively surrounded together by one shielding cover 26. The remaining other parts such as the vacuum tubes of the beam transmitting device may be alternatively surrounded by the shielding cover, thereby preventing neutrons and other radioactive rays from leaking from the beam transmitting device.

The boron neutron capture therapy system 100 may further include a preparation room, a control room, and another space used to assist in treatment. Each irradiation room may be provided with one preparation room used for preparation work, for example, securing a patient to a treatment table, injecting boron-containing pharmaceuticals, and simulating a treatment plan before treatment with irradiation. A connecting passage is disposed between the preparation room and the irradiation room. After the preparation work is completed, the patient is directly pushed into the irradiation room or a control mechanism controls automatic entry of the patient into the irradiation room by a rail. The preparation room and the connecting passage may also be closed by a shielding wall. The preparation room further has a shielding door. The control room is configured to control the accelerator, the beam transmitting device, the treatment table, and the like, and control and manage the entire irradiation process. A manager may further simultaneously monitor a plurality of the irradiation rooms in the control room.

It should be understood that, in this embodiment, the shielding walls (including concrete walls W), the shielding door, the shielding assembly, and the shielding cover may all have other thicknesses or densities or may be replaced with other materials.

Although the illustrative embodiments of the present invention have been described above in order to enable those skilled in the art to understand the present invention, it should be understood that the present invention is not to be limited the scope of the embodiments. For those skilled in the art, as long as various changes are within the spirit and scope as defined in the present invention and the appended claims, these changes are obvious and within the scope of protection claimed by the present invention.

What is claimed is:

1. A neutron capture therapy system, comprising:
an accelerator configured to accelerate charged particles to generate a charged particle beam;
a beam transmitting device configured to transmit the charged particle beam generated by the accelerator, wherein the beam transmitting device comprises a first transmitting device connected to the accelerator, a beam direction conversion device configured to convert a traveling direction of the charged particle beam, a second transmitting device, a third transmitting device, and a fourth transmitting device; and
a neutron beam generating device configured to generate a therapeutic neutron beam, wherein the charged particle beam is transmitted to the neutron beam generating device through the beam transmitting device, and the neutron beam generating device comprises a first neutron beam generating device, a second neutron beam generating device, and a third neutron beam generating device;
wherein the second transmitting device, the third transmitting device and the fourth transmitting device respectively transmit the charged particle beam from the beam direction conversion device to the first neutron beam generating device, the second neutron beam generating device, and the third neutron beam generating device, and
wherein two of the first transmitting device, the third transmitting device, and the fourth transmitting device define a first plane, the first transmitting device and the second transmitting device define a second plane, and the first plane is different from the second plane.

2. The neutron capture therapy system according to claim 1, wherein the first transmitting device transmits the charged particle beam in an X-axis direction, and transmission directions of the third transmitting device and the fourth transmitting device are on an XY plane and form an angle greater than 0 degrees.

3. The neutron capture therapy system according to claim 2, wherein the second transmitting device transmits the charged particle beam in a Z-axis direction, and the transmission directions of the third transmitting device and the fourth transmitting device and a transmission direction of the first transmitting device form a "Y" shape.

4. The neutron capture therapy system according to claim 1, wherein the first neutron beam generating device, the second neutron beam generating device, and the third neutron beam generating device are respectively disposed along transmission directions of the second transmitting device, the third transmitting device, and the fourth transmitting device, directions of neutron beams generated by the first neutron beam generating device, the second neutron beam generating device, and the third neutron beam generating device are respectively same as the transmission directions of the second transmitting device, the third transmitting device, and the fourth transmitting device, so that the directions of the neutron beams generated by the second neutron beam generating device and the third neutron beam generating device are on a same plane, and the direction of the neutron beam generated by the first neutron beam generating device is substantially perpendicular to the plane.

5. The neutron capture therapy system according to claim 1, further comprising a beam dump configured to check an output of the charged particle beam before treatment, wherein the beam direction conversion device comprises a first beam direction conversion assembly and a second beam direction conversion assembly, the beam transmitting device further comprises a fifth transmitting device that connects the first beam direction conversion assembly and the second beam direction conversion assembly, the second transmitting device connects the first beam direction conversion assembly and the first neutron beam generating device, the third transmitting device connects the second beam direction conversion assembly and the second neutron beam generating device, and the fourth transmitting device connects the second beam direction conversion assembly and the third neutron beam generating device, each of the first beam direction conversion assembly and the second beam direction conversion assembly comprises a deflection electromagnet configured to deflect the charged particle beam and a switch electromagnet configured to control the traveling direction of the charged particle beam, the first beam direction conversion assembly or the second beam direction conversion assembly guides the charged particle beam to the beam dump, each of the first transmitting device, the second transmitting device, the third transmitting device, the fourth transmitting device, and the fifth transmitting device comprises a beam adjuster for the charged particle beam, and each of the second transmitting device, the third transmitting device, and the fourth transmitting device comprises a current monitor and a charged particle beam scanner.

6. The neutron capture therapy system according to claim 1, further comprising an irradiation room, wherein a patient receives treatment of neutron beam irradiation in the irradiation room, the irradiation room comprises a first irradiation room, a second irradiation room, and a third irradiation room that respectively correspond to the first neutron beam generating device, the second neutron beam generating device, and the third neutron beam generating device, and the first irradiation room, the second irradiation room, and the third irradiation room are respectively disposed along transmission directions of the second transmitting device, the third transmitting device, and the fourth transmitting device.

7. The neutron capture therapy system according to claim 6, wherein further comprising a charged particle beam generation room, wherein the charged particle beam generation room accommodates the accelerator and at least part of the beam transmitting device and comprises an accelerator room and a beam transmission room, the first transmitting device extends from the accelerator room to the beam transmission room, at least part of the second neutron beam generating device and at least part of the third neutron beam generating device are respectively buried in partition walls that respectively separate the second irradiation room and the third irradiation room from the beam transmission room, the third transmitting device and the fourth transmitting device respectively extend from the beam transmission room to the second neutron beam generating device and the third neutron beam generating device, the first neutron beam generating device is located in the first irradiation room, the second transmitting device extends from the beam transmission room to the first irradiation room through the floor, and the neutron capture therapy system further comprises a preparation room and a control room.

8. A neutron capture therapy system comprising:
an accelerator configured to accelerate charged particles to generate a charged particle beam;
a beam transmitting device configured to transmit the charged particle beam generated by the accelerator;
a charged particle beam generation room, wherein the charged particle beam generation room accommodates the accelerator and at least part of the beam transmitting device, and the charged particle beam generation room comprises an accelerator room and a beam transmission room;
a first neutron beam generating device configured to generate a therapeutic neutron beam, wherein the charged particle beam is transmitted to the first neutron beam generating device through the beam transmitting device;
a first irradiation room, wherein a patient receives treatment of neutron beam irradiation in the first irradiation room, and at least part of the first neutron beam generating device is buried in a first partition wall that separates the first irradiation room from the charged particle beam generation room; and
a first shielding wall disposed between the first neutron beam generating device and the accelerator to protect an operator from irradiation by neutrons and other radioactive rays leaked from the first neutron beam generating device during repair and maintenance of the accelerator and reduce reactions in which the accelerator is activated, wherein the first shielding wall is disposed in the charged particle beam generation room, and the first shielding wall is a partition wall between the accelerator room and the beam transmission room,
wherein the beam transmitting device comprises a first transmitting device that is connected to the accelerator and extends from the accelerator room to the beam transmission room and a second transmitting device that extends from the beam transmission room to the first neutron beam generating device and transmits the charged particle beam to the first neutron beam generating device, the first partition wall is a partition wall that separates the first irradiation room from the beam transmission room, and the first transmitting device passes through the first shielding wall.

9. The neutron capture therapy system according to claim 8, wherein the first transmitting device comprises a first beam direction conversion assembly and a second beam direction conversion assembly configured to switch a traveling direction of the charged particle beam, a third transmitting device that connects the accelerator and the first beam direction conversion assembly, a fourth transmitting device that connects the first beam direction conversion assembly and the second beam direction conversion assembly, and a fifth transmitting device that connects the second transmitting device and the second beam direction conversion assembly, the first shielding wall is disposed between the accelerator and the first beam direction conversion assembly, and the third transmitting device passes through the first shielding wall; or the first shielding wall is disposed between the second beam direction conversion assembly and the first neutron beam generating device, and the fifth transmitting device passes through the first shielding wall; or the first shielding wall is disposed between the first beam direction conversion assembly and the second beam direction conversion assembly, and the fourth transmitting device passes through the first shielding wall.

10. The neutron capture therapy system according to claim 9, further comprising a second neutron beam generating device and a second irradiation room, wherein at least part of the second neutron beam generating device is buried in a second partition wall that separates the second irradiation room from the beam transmission room, the beam transmitting device further comprises a sixth transmitting device that extends from the beam transmission room to the second neutron beam generating device and transmits the charged particle beam to the second neutron beam generating device, the first transmitting device further comprises a seventh transmitting device that connects the sixth transmitting device and the second beam direction conversion assembly, when the first shielding wall is disposed between the second beam direction conversion assembly and the first neutron beam generating device, the seventh transmitting device also passes through the first shielding wall, each of the first beam direction conversion assembly and the second beam direction conversion assembly comprises a deflection electromagnet for deflecting the charged particle beam and a switch electromagnet for controlling the traveling direction of the charged particle beam, the neutron capture therapy system further comprises a beam dump configured to check an output of the charged particle beam before treatment, the first beam direction conversion assembly or the second beam direction conversion assembly guides the charged particle beam to the beam dump, each of the first transmitting device, the second transmitting device, and the sixth transmitting device comprises a beam adjuster for the charged particle beam, and each of the second transmitting device and the sixth transmitting device comprises a current monitor and a charged particle beam scanner.

11. The neutron capture therapy system according to claim 8, wherein a second shielding wall is disposed between the first partition wall and the first shielding wall.

12. The neutron capture therapy system according to claim 8, wherein a shielding door is disposed in the first shielding wall, and the shielding door comprises a primary shielding door and a secondary shielding door or only comprises a primary shielding door or secondary shielding door.

13. A neutron capture therapy system comprising:
an accelerator configured to accelerate charged particles to generate a charged particle beam;
a beam transmitting device configured to transmit the charged particle beam generated by the accelerator, wherein the beam transmitting device comprises a shielding assembly for preventing neutrons and other radioactive rays from leaking from the beam transmitting device, a first transmitting device connected to the accelerator, a beam direction conversion device configured to switch a traveling direction of the charged particle beam, and a second transmitting device configured to transmit the charged particle beam to the neutron beam generating device, and the shielding assembly is a shielding cover surrounding the beam direction conversion device; and a neutron beam generating device configured to generate a therapeutic neutron beam, wherein the charged particle beam is transmitted to the neutron beam generating device through the beam transmitting device.

14. The neutron capture therapy system according to claim 13, further comprising the a beam dump configured to check an output of the charged particle beam before treatment, wherein the beam direction conversion device comprises a first beam direction conversion assembly and a second beam direction conversion assembly, the beam transmitting device further comprises a third transmitting device that connects the first beam direction conversion assembly and the second beam direction conversion assembly, and the shielding cover is two cover bodies that respectively surround the first beam direction conversion assembly and the second beam direction conversion assembly, each of the first beam direction conversion assembly and the second beam direction conversion assembly comprises a deflection electromagnet for deflecting the charged particle beam and a switch electromagnet for controlling the traveling direction of the charged particle beam, the first beam direction conversion assembly or the second beam direction conversion assembly guides the charged particle beam to the beam dump, each of the first transmitting device, the second transmitting device, and the third transmitting device comprises a beam adjuster for the charged particle beam, and the second transmitting device comprises a current monitor and a charged particle beam scanner.

15. The neutron capture therapy system according to claim 14, wherein the neutron beam generating device comprises three neutron beam generating device, the second transmitting device comprises a fourth transmitting device, a fifth transmitting device, and a sixth transmitting device that respectively transmit the charged particle beam to the three neutron beam generating device, the first transmitting device branches into the third transmitting device and the fourth transmitting device in the first beam direction conversion assembly, and the third transmitting device branches into the fifth transmitting device and the sixth transmitting device in the second beam direction conversion assembly.

16. The neutron capture therapy system according to claim 13, further comprising a charged particle beam generation room and an irradiation room, wherein the charged particle beam generation room accommodates the accelerator and at least part of the beam transmitting device, a patient receives treatment of neutron beam irradiation in the irradiation room, and at least part of the neutron beam generating device is buried in a partition wall that separates the irradiation room from the charged particle beam generation room.

17. The neutron capture therapy system according to claim 16, wherein the charged particle beam generation room comprises an accelerator room and a beam transmission room, the first transmitting device extends from the accelerator room to the beam transmission room, the second transmitting device extends from the beam transmission room to the neutron beam generating device, and the beam direction conversion device and the shielding cover are accommodated in the beam transmission room.

* * * * *